US012583880B2

United States Patent

(12) United States Patent
Khanzhin et al.

(10) Patent No.: US 12,583,880 B2
(45) Date of Patent: Mar. 24, 2026

(54) SEPARATION OF OLIGOSACCHARIDES

(71) Applicant: Glycom A/S, Hørsholm (DK)

(72) Inventors: Nikolay Khanzhin, Humlebæk (DK); Markus Jondelius Hederos, Trelleborg (SE); Pierre Chassagne, Beaumont (FR)

(73) Assignee: Glycom A/S, Hørsholm (DK)

( * ) Notice: Subject to any disclaimer, the term of this patent is extended or adjusted under 35 U.S.C. 154(b) by 761 days.

(21) Appl. No.: 17/415,274

(22) PCT Filed: Dec. 19, 2019

(86) PCT No.: PCT/IB2019/061093

§ 371 (c)(1),
(2) Date: Jun. 17, 2021

(87) PCT Pub. No.: WO2020/128945

PCT Pub. Date: Jun. 25, 2020

(65) Prior Publication Data

US 2022/0056065 A1 Feb. 24, 2022

(30) Foreign Application Priority Data

Dec. 19, 2018 (DK) .......................... PA 2018 01036

(51) Int. Cl.
*C07H 1/06* (2006.01)
*B01D 15/12* (2006.01)
*C12P 19/26* (2006.01)

(52) U.S. Cl.
CPC ............ *C07H 1/06* (2013.01); *B01D 15/125* (2013.01); *C12P 19/26* (2013.01)

(58) Field of Classification Search
CPC ............ C07H 1/06; C07H 3/06; B01J 20/285
See application file for complete search history.

(56) References Cited

U.S. PATENT DOCUMENTS

| | | | |
|---|---|---|---|
| 2005/0065290 | A1 | 3/2005 | Shah |
| 2006/0127987 | A1 | 6/2006 | Han et al. |

FOREIGN PATENT DOCUMENTS

| | | | | |
|---|---|---|---|---|
| EP | 1405856 | A1 | 4/2004 | |
| EP | 2896628 | A1 | 7/2015 | |
| JP | S61130297 | A | 6/1986 | |
| JP | S62120394 | A | 6/1987 | |
| JP | 2008228640 | A | 10/2008 | |
| JP | 2009291120 | A | 12/2009 | |
| WO | 0104341 | A1 | 1/2001 | |
| WO | 2015032412 | A1 | 3/2015 | |
| WO | 2015049331 | A1 | 4/2015 | |
| WO | 2015106943 | A1 | 7/2015 | |
| WO | WO-2017071715 | A1 * | 5/2017 | ............ A23L 33/15 |
| WO | 2017182965 | A1 | 10/2017 | |
| WO | 2017221208 | A1 | 12/2017 | |

OTHER PUBLICATIONS

Product Data Sheet. Purosorb(TM) 7. Purolite.com. Web. 2018. (Year: 2018).*
Han, Y., et al. Journal of Environmental Chemical Engineering. 8 (2020), 104098. (Year: 2020).*
Product Data Sheet. Sepabeads(TM) SP207. Mitsubishi Chemical Corporation. Diaion.com. Web. 2024. (Year: 2024).*
Cataldi, T. R. I., et al. Fresenius J. Anal. Chem. 2000, 368 :739-758. (Year: 2000).*
Huck, C., E., et al. Chem. Eng. Technol. 2005, 28(12), pp. 1457-1472. (Year: 2005).*
Chen, X., "Human Milk Oligosaccharides (HMOS): Structure, Function, and Enzyme-Catalyzed Synthesis," Advances in Carbohydrate Chemistry and Biochemistry, 2015, vol. 72, pp. 113-190.
Gebus, C., et al., "Synthesis of alpha-galactosyl epitopes by metabolically engineered *Escherichia coli*," Carbohydrate Research, 2012, vol. 361, pp. 83-90.
Priem, B., et al., "A new fermentation process allows large-scale production of human milk oligosaccharides by metabolically engineered bacteria," Glycobiology, 2002, vol. 12(4), pp. 235-240.
Urashima, T., et al. (2011) Nutrition and Diet Research Progress: Milk Oligosaccharides. New York: Nova Science Publishers, Inc. 92 pages.

* cited by examiner

*Primary Examiner* — Andrea Olson
*Assistant Examiner* — Samuel L Galster
(74) *Attorney, Agent, or Firm* — Neal, Gerber & Eisenberg LLP

(57) ABSTRACT

The invention relates to a method for the separation of two hydrophilic neutral oligosaccharides from each other with a chromatography on a bromine functionalized polystyrene cross-linked with divinylbenzene (BPS-DVB) stationary medium.

11 Claims, No Drawings

SEPARATION OF OLIGOSACCHARIDES

CROSS-REFERENCE TO RELATED APPLICATION

This application is a national stage entry pursuant to 35 U.S.C. § 371 of International Application No. PCT/IB2019/061093, filed on Dec. 19, 2019, which claims priority to Denmark Patent Application No. PA 2018 01036 filed on Dec. 19, 2018, the contents of all of which are fully incorporated herein by reference.

FIELD OF THE INVENTION

This invention relates to a method for the separation of two hydrophilic neutral oligosaccharides from each other, preferably at least two neutral human milk oligosaccharides (HMOs), produced by a fermentation or enzymatic process. In particular, one of the at least two neutral oligosaccharides has higher molecular weight than the other, and they show partition on a hydrophobic stationary phase.

BACKGROUND OF THE INVENTION

In recent years, efforts have increasingly been made to produce industrially complex carbohydrates, such as secreted oligosaccharides. This has been due to the roles of such compounds in numerous biological processes in living organisms. Secreted oligosaccharides, such as human milk oligosaccharides (HMOs), have become particularly important commercial targets for nutrition and therapeutic applications. Human milk oligosaccharides have become of great interest in the past few years due to their important functions in human development. To date, the structures of more than 140 HMOs have been determined, and considerably more are probably present in human milk (Urashima et al.: *Milk oligosaccharides*, Nova Biomedical Books, 2011; Chen *Adv. Carbohydr. Chem. Biochem.* 72, 113 (2015)).

Low cost ways have been sought for making industrial quantities of as many as possible of the HMOs, so that their uses in nutritional and therapeutic formulations for infants, children and adults could be studied, developed and exploited by researchers and companies worldwide. Currently, HMOs have been produced enzymatically or, mostly, by fermentation using transformed one-cell organisms, particularly *E. coli*. These methods, however, provide the HMO of interest accompanied by another oligosaccharide/HMO by-products. Typically, 2'-FL is mostly accompanied by DFL and/or 3-FL (see e.g. EP-A-2896628, WO 2015/032412, WO 2015/106943), LNnT fermentation broths comprise lacto-N-triose II (GlcNAcβ1-3Galβ1-4Glc) and higher oligosaccharises like pLNnH (Galβ1-4GlcNAcβ1-3Galβ1-4GlcNAcβ1-3Galβ1-4Glc) (see e.g. WO 01/04341, Priem et al. *Glycobiology* 12, 235 (2002), Gebus et al. *Carbohydr. Res.* 361, 83 (2012), WO 2017/182965) and LNT is contaminated by lacto-N-triose II and higher oligosaccharises like pLNH II (Galβ1-3 GlcNAcβ1-3 Galβ1-3 G1 cNAcβ1-3 Galβ1-4Glc) (see e.g. WO 2015/049331, WO 2017/182965).

WO 2017/182965 proposes a process how to separate an oligosaccharide mixture made by fermentation from the non-carbohydrate components of a broth (such as biomass, acids, bases, organic and inorganic salts, proteins, protein fragments, DNA, endotoxins, biogenic amines, colorizing bodies, etc.), the process comprises ultrafiltration, nanofiltration and application of ion exchange resins comprising a treatment with a strong cation exchange resin in $H^+$-form directly followed by a treatment with a weak anion exchange resin in free base form. This method, however, does not separate the oligosaccharide components from each other significantly.

EP-A-2896628 describes a process for 2'-FL purification from fermentation broth comprising the following steps: ultrafiltration, strong cation exchange resin treatment ($H^+$-form), neutralization, strong anion exchange resin treatment ($Cl^-$-form), neutralization, nanofiltration/diafiltration, active charcoal treatment, electrodialysis, strong cation exchange resin treatment ($Na^+$-form), strong anion exchange resin treatment ($Cl^-$-form), active charcoal treatment and electrodialysis, emphasizing that no chromatography is employed. Although the method provides 2'-FL with a purity of 94-94.5% (by HPLC), the application is silent about whether the amounts of major carbohydrate contaminants (such as 3-FL, DFL and lactose) present in the final product in ≈5% are reduced by the process.

To separate structurally close oligosaccharides from each other is a difficult task due to their very similar properties. Gel filtration is certainly an option (see. e.g. Priem et al. *Glycobiology* 12, 235 (2002)), however it is considered to be a laboratory method rather than an industrially profitable process.

WO 2015/049331 discloses a method for LNT purification from fermentation broth comprising the following operation sequence: to provide a clear particle free solution, electrodialysis/nanofiltration, first simulated moving bed (SMB) strong cation exchange resin chromatography, electrodialysis, ultrafiltration. Using certain SMB parameters, LNT and larger neutral oligosaccharides are fractioned in the raffinate, whereas smaller carbohydrates (lactose, monosaccharides) are enriched in the extract fraction. To further purify LNT from higher oligosaccharides, a second SMB chromatography is performed with different parameters resulting in the LNT enrichment in the extract fraction.

However, alternative, more efficient, robust and/or cost-effective procedures, suitable for industrial scale-up, for isolating and purifying LNT, LNnT and other neutral HMOs from accompanying carbohydrate by-products that are often made in the fermentation process are still needed.

SUMMARY OF THE INVENTION

In accordance with this invention, a method is provided for separating a first hydrophilic neutral oligosaccharide from a second hydrophilic neutral oligosaccharide in an aqueous medium, comprising treating the aqueous medium by chromatography using a hydrophobic stationary phase which is a polystyrene cross-linked with divinylbenzene (PS-DVB) and functionalized with bromine on the aromatic ring. When the aqueous medium is contacted with the bromine functionalized PS-DVB (BPS-DVB) hydrophobic stationary chromatography medium, one of the oligosaccharides is retained by the stationary solid phase more than the other, thereby the enriched or separated fractions of the respective oligosaccharides can be obtained.

In one embodiment, the number of the monosaccharide units in one of the hydrophilic neutral oligosaccharides is higher than that in the other hydrophilic neutral oligosaccharide.

In other embodiment, one of the hydrophilic neutral oligosaccharides consists of at least two monosaccharide units more than the other.

In other embodiment, one of the hydrophilic neutral oligosaccharides comprises at least one N-acetylglucosaminyl (G1cNAc)- or N-acetylgalactosaminyl (Ga1NAc)-moiety whereas the other does not.

In other embodiment, one of the hydrophilic neutral oligosaccharides comprises more G1cNAc- or Ga1NAc-moieties than the other.

In one embodiment, at least one of the hydrophilic neutral oligosaccharides is a human milk oligosaccharide or a precursor thereof.

In one embodiment, the first and the second hydrophilic neutral oligosaccharide are human milk oligosaccharides or precursors thereof.

In one embodiment, the first and the second hydrophilic neutral oligosaccharide are human milk oligosaccharides, one of them consisting of at least two monosaccharide units more than the other.

In one embodiment, the first and the second hydrophilic neutral oligosaccharide are human milk oligosaccharides, one of them being a tetrasaccharide and the other being a hexasaccharide.

In one embodiment, at least one of the hydrophilic neutral oligosaccharides is human milk oligosaccharide that contains a G1cNAc-moiety.

In one embodiment, the first and the second hydrophilic neutral oligosaccharide are human milk oligosaccharides and both comprise a G1cNAc-moiety.

In one embodiment, the first and the second hydrophilic neutral oligosaccharide are human milk oligosaccharides, both comprise a G1cNAc-moiety and one of them consists of at least two monosaccharide units more than the other.

In one embodiment, the first and the second hydrophilic neutral oligosaccharides are human milk oligosaccharides and one of them comprises more G1cNAc-moiety than the other.

In one embodiment, the first and the second hydrophilic neutral oligosaccharides are human milk oligosaccharides, both comprise a G1cNAc-moiety and one of them comprises more G1cNAc-moiety than the other.

In one embodiment, the first and the second hydrophilic neutral oligosaccharides are human milk oligosaccharides, one of them consists of at least two monosaccharide units more than the other and the higher oligosaccharide (that is the one having more monosaccharide units) comprises more G1cNAc-moiety than the lower oligosaccharide.

In one embodiment, the first and the second hydrophilic neutral oligosaccharides are human milk oligosaccharides, one of them is a hexasaccharide comprising two, preferably exactly two, G1cNAc-moieties and the other is a tetrasaccharide comprising one, preferably exactly one, G1cNAc-moiety.

In one embodiment, the human milk oligosaccharides or precursors thereof are produced intracellularly by fermentation, particularly by *E. coli* in an aqueous culture medium and then secreted into the aqueous culture medium.

In one embodiment, before treating the aqueous medium comprising the human milk oligosaccharides or precursors thereof by the BPS-DVB chromatography, one or both of the following steps are carried out:

a) the aqueous medium is clarified to remove particulates and contaminants and advantageously also cell components and any insoluble metabolites and debris from a fermentation process; and
b) substantially all proteins are removed from the aqueous medium, advantageously after the aqueous medium is clarified in step a).

In one embodiment, the first and second oligosaccharides comprise LNnT and pLNnH.

In one embodiment, the first and second oligosaccharides comprise LNT and pLNH II.

DETAILED DESCRIPTION

Typically, the application of highly hydrophobic stationary chromatographic medium (reverse phase chromatography, RPC) is not suitable for separating highly polar oligosaccharides (see e.g. WO 2017/221208). The present inventors surprisingly found that the RPC may be applicable for this task, provided that the solid chromatographic phase is composed of polystyrene cross-linked with divinylbenzene and functionalized with bromine on the aromatic ring (BPS-DVB).

In accordance with this invention, a method is provided for separating, at least partially, a first hydrophilic neutral oligosaccharide from a second hydrophilic neutral oligosaccharide, the oligosaccharides being preferably produced by a fermentation or in an ex vivo enzymatic process, the method comprising subjecting an aqueous solution comprising the first and the second oligosaccharide to chromatography on a bromine functionalized polystyrene cross-linked with divinylbenzene (BPS-DVB) stationary medium.

Preferably, the level of bromination of the BPS-DVB resin is about 25-61 w/w %, for example 25-35 w/w %.

The above chromatographic separation process proved to be robust both as a batch process and in multi-column set-up, spanning from R&D lab through pilot plant to industrial full-scale. The solid phase and the associated chromatographic run can be done in a fashion where a gradient is applied using e.g. aqueous alcohol, but can also be run completely without organic solvents (pure water). The process well-functions at high temperature (e.g. up to 60° C.) which provides a benefit in terms of reduced risk of microbial growth and increased productivity. In addition, the solid phase can be fully regenerated using e.g. aqueous acetic acid and thereby very suitable for food-related processing.

In this invention, the term "reversed-phase chromatography" or RPC, preferably means any chromatographic method that uses a hydrophobic stationary (i.e. packed) or suspended phase and a polar (i.e. aqueous) mobile phase comprising the components to be separated.

The term "hydrophilic neutral oligosaccharide" preferably means a sugar polymer containing at least two monosaccharide units, i.e. a di-, tri-, tetra- or higher oligosaccharide. The oligosaccharide can have a linear or branched structure containing the monosaccharide units that are linked to each other by interglycosidic linkages. Preferably, the oligosaccharide consists of two to eight, more preferably two to six, monosaccharide moieties. Obviously, the monosaccharide units making up the oligosaccharide are neutral monosaccharides and cannot be acidic monosaccharides such as aldonic acid, keto-aldonic acid (like sialic acid), aldaric acid, alduronic acid or basic monosaccharide moieties like one with free amino group. The hydroxyl groups of the neutral monosaccharide units are not protected, consequently the oligosaccharide made up by the monosaccharides is unprotected, too. The neutral monosaccharide unit can be selected from any 5-9, preferably 5-6, carbon atom containing monosaccharide consisting of aldoses (e.g. D-glucose, D-galactose, D-mannose, D-ribose, D-arabinose, L-arabinose, D-xylose, etc.), ketoses (e.g. D-fructose, D-sorbose, D-tagatose, etc.), deoxysugars (e.g. L-rhamnose, L-fucose, etc.) and N-acetylated deoxy-aminosugars (e.g. N-acetylglucosamine, N-acetylmannosamine, N-acetylgalactosamine, etc.).

The term "bromine functionalized polystyrene cross-linked with divinylbenzene", "polystyrene cross-linked with divinylbenzene and functionalized with bromine" or "BPS-DVB" refers to a modified copolymer of styrene and divinylbenzene in which at least a part of the styrene monomer is replaced by bromostyrene (wherein the bromine is on the aromatic ring) or the polystyrene-divinylbenzene copolymer is brominated with a bromination agent.

The term "$C_1$-$C_4$ alcohol" means an alkyl alcohol of 1 to 4 carbon atoms, such as methanol, ethanol, propanol or butanol. Preferred $C_1$-$C_4$ alcohol is isopropanol.

The term "aqueous medium [from a fermentation or enzymatic process]" preferably means an aqueous suspension resulting from an enzymatic or fermentation process for producing at least one hydrophilic neutral oligosaccharide.

The term "clarified aqueous medium" preferably means an aqueous medium, e.g. that of an enzymatic process or a fermentation broth, which has been treated to remove suspended particulates and contaminants from the process, particularly cells, cell components, insoluble metabolites and debris from a fermentation process, that could interfere with the later step(s) of the purification. Such a clarification treatment can be carried out in a conventional manner by centrifugation, flocculation, flocculation with optional ultrasonic treatment, gravity filtration, microfiltration, ultrafiltration, foam separation or vacuum filtration (e.g., through a ceramic filter which may include a Celite™ filter aid).

The term "protein-free aqueous medium" preferably means an aqueous medium, e.g. that of an enzymatic process or a fermentation broth, which has been treated to remove substantially all the proteins, and preferably as well as peptides, amino acids, RNA, DNA and fragments thereof, as well as endotoxins and glycolipids that could interfere with the later step(s) of purification. Such removal of proteins, amino acids, RNA and DNA can be accomplished in a conventional manner by ion exchange chromatography, affinity chromatography, ultrafiltration, nanofiltration or size exclusion chromatography.

The term "higher oligosaccharide" means that its degree of polymerization is higher than that of another oligosaccharide, that is it comprises more monosaccharide units than the other.

The term "lower oligosaccharide" means that its degree of polymerization is lower than that of another oligosaccharide, that is it comprises less monosaccharide units than the other.

The claimed separation method can be carried out in a conventional manner. The aqueous solution comprising the first and the second hydrophilic neutral oligosaccharide is used as the mobile phase in the chromatography. An organic solvent, preferably a $C_1$-$C_4$ alcohol, may be added to the aqueous solution. The pH of the aqueous solution is preferably between 3 to 8, more preferably between 4 to 7. If necessary, the pH can be adjusted to the required value in a conventional manner by addition of an aqueous solution of an acid, a base or a buffer. The separation can be easily done by using a conventional chromatographic column or container of laboratory or industrial scale, in which the BPS-DVB resin can be either packed or suspended (e.g. as beads). Preferably, separation method is performed in a column.

The degree of separation depends on many parameters, such as the nature of the eluent, flow/elution rate, volumes of fractions collected, mass of the first and the second oligosaccharide relative to the resin mass or resin bed volume, etc. These parameters can be optimized with routine skills. The term "separation" means a full separation of the first and the second oligosaccharide from each other, that is they are collected and isolated from the fractions in pure form not containing each other. Also, the term "separation" means a partial separation wherein at least one of the oligosaccharides can be obtained from at least one fraction in pure form or the ratio of the first and the second oligosaccharide in the fraction(s) is different than that in the feed solution, thereby one of the oligosaccharides is enriched.

After carrying out the separation of the first hydrophilic neutral oligosaccharide from the second hydrophilic neutral oligosaccharide by means of BPS-DVB chromatography as disclosed above, the purified or enriched first and/or second oligosaccharide(s) can then be isolated from the aqueous fraction(s) in which it is (they are) collected in a conventional manner, e.g. by evaporation, crystallization, freeze-drying or spray-drying.

Preferably, the chromatography on the BPS-DVB stationary medium comprises:

loading the aqueous solution comprising the first and the second hydrophilic neutral oligosaccharide onto the BPS-DVB medium, eluting with water optionally containing a $C_1$-$C_4$ alcohol, and then collecting the fractions comprising or enriched in one of the oligosaccharides.

After chromatography, the BPS-DVB medium can be regenerated by elution with water containing water-miscible organic solvents and recycled.

Also preferably, the aqueous solution comprising the first and the second hydrophilic neutral oligosaccharide is a pre-treated fermentation broth or aqueous reaction medium in which the first and the second oligosaccharides produced/comprised.

One aspect of this method involves separating the first and the second hydrophilic neutral oligosaccharide from each other, at least partially, the oligosaccharides being produced intracellularly by fermentation, preferably by *E. coli*, in an aqueous culture medium and then secreted, transported or brought into the aqueous culture medium. The method may involve, before the BPS-DVB chromatography, the following pre-treatment steps:

a) clarifying the aqueous culture medium to remove therefrom particulates and contaminants, preferably also cells, cell components and any insoluble metabolites and debris from a fermentation process, to provide a clarified aqueous medium, and/or b) removing substantially all proteins from the aqueous medium, preferably from the clarified aqueous medium of step a), to provide a protein-free aqueous medium, and/or c) removing salts and charged components from the aqueous culture medium, from the clarified aqueous medium of step a), or from the protein-free aqueous medium of step b).

Accordingly, the clarified aqueous medium from step a), the protein-free aqueous medium from step b) or the aqueous medium obtained in step c) is loaded onto the BPS-DVB resin.

Another aspect of the method relates to separating a first and the second hydrophilic neutral oligosaccharide from each other, at least partially, at least one of the oligosaccharides being produced enzymatically ex vivo in an aqueous medium. An ex vivo enzymatic reaction mixture typically contains, besides the oligosaccharides of interest produced, proteins, protein fragments, inorganic salts, unreacted carbohydrate acceptor (typically lactose) or donor, sugar-like by-products, carbohydrate leaving group (typically a mono- or disaccharide), etc. The method may involve, before the BPS-DVB chromatography, the following pre-treatment steps: ultrafiltration (UF), nanofiltration (NF) and optional active charcoal (AC) treatment. UF comprises separating high molecular weight suspended solids, typically proteins or protein fragments, from the soluble components of the aqueous medium which pass through the ultrafiltration membrane in the permeate. This UF permeate (UFP) is an aqueous solution containing the produced oligosaccharide accompanied by other carbohydrate products. The NF step may follow the UF step or the optional step of AC treatment; this step may advantageously be used to concentrate the previously treated aqueous medium comprising the produced oligosaccharide accompanied by other carbohydrate products and/or to remove ions, mainly monovalent ions, and organic materials having a molecular weight lower than that of the oligosaccharide product, such as monosaccharides. In this regard, the produced oligosaccharide accompanied by other oligosaccharides is accumulated in the NF retentate (NFR). The NF can be combined with diafiltration with water in order to remove permeable molecules more effectively, e.g. until the conductivity of the permeate showing no or very low presence of salts. The optional AC step may follow the UF step, NF step or the BPS-DVB resin. The AC treatment helps to remove or at least reduce the amount of colorizing agents and/or water soluble contaminants, such as salts, if required.

In one embodiment of the claimed separation process, an aqueous medium, which can come directly from an enzymatic or preferably a fermentation process, particularly of *E. coli* or yeast, and which contains a first and the second hydrophilic neutral oligosaccharide, is treated by the following steps:

1) clarifying the aqueous medium to remove suspended particulates and contaminants, particularly cells, cell components, insoluble metabolites and debris from a fermentation process; then
2) removing substantially all the proteins, as well as peptides, amino acids, RNA and DNA and any endotoxins and glycolipids that could interfere with the subsequent purification step, from the aqueous solution obtained in step 1); and then
3) separating the first and the second oligosaccharide from the aqueous solution obtained in step 2) by chromatography on BPS-DVB.

In step 1), the aqueous medium, which contains first and the second oligosaccharide, is clarified in a conventional manner, e.g. by centrifugation or filtration. Preferably the aqueous medium is first flocculated and then centrifuged or filtered to remove any remaining insoluble particulates and contaminants, as well as cells and cell components and insoluble metabolites and debris.

In step 2), proteins and related impurities are removed from the aqueous medium in a conventional manner, e.g., by ultrafiltration, nanofiltration, tangential flow high-performance filtration, tangential flow ultrafiltration, affinity chromatography, ion exchange chromatography, hydrophobic interaction chromatography, gel filtration, size exclusion chromatography, active charcoal treatment. The active charcoal treatment helps to remove or at least reduce the amount of colorizing agents and/or water soluble contaminants, such as salts, if required. Ion exchange chromatography efficiently removes charged components such as salts, colour bodies, proteins, amino acids, lipids and DNAs.

In the method of separating a first hydrophilic neutral oligosaccharide from a second hydrophilic neutral oligosaccharide by chromatography on BPS-DVB described above, including any preferred and/or disclosed embodiments, the first and the second oligosaccharide differ from each other in at least one structural feature, e.g. at least one monosaccharide unit is different, the number of monosaccharide units is different or the orientation of at least one of the interglycosidic linkages is different (whether it is α or β). In one embodiment, one of the oligosaccharides consists of one monosaccharides units more than the other. In other embodiment, one of the oligosaccharides consists of two or at least two monosaccharides units more than the other, for example one of the oligosaccharides is a trisaccharide and the other is a pentasaccharide, or one of the oligosaccharides is a tetrasaccharide and the other is a hexasaccharide. In other embodiment, one of the oligosaccharides comprises at least one GlcNAc- or GalNAc-unit, preferably a GlcNAc-unit, whereas the other does not. In other embodiment, one of the oligosaccharides comprises more GlcNAc- or GalNAc-units, preferably a GlcNAc-units, than the other.

Preferably, one of the oligosaccharides comprises the structure of the other oligosaccharide, that is one of the oligosaccharides is a glycosylated derivative of the other. More preferably, the glycosylation comprises to attach at least two monosaccharide units. Even more preferably, the structure that is commonly shared by the first and the second oligosaccharide is lactose or its glycosylated derivatives.

Also preferably, the first and the second hydrophilic neutral oligosaccharide comprise a lactose (Galβ1-4Glc) moiety at the reducing end. More preferably, the first and the hydrophilic neutral second oligosaccharide is characterized by the following formula 1

1

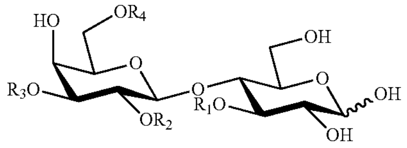

$R_1$ is fucosyl or H,
$R_2$ is fucosyl or H,
$R_3$ is selected from H, N-acetyl-glucosaminyl, N-acetyl-lactosaminyl and lacto-N-biosyl groups, wherein the N-acetyl-lactosaminyl group or the lacto-N-biosyl group can carry a glycosyl residue comprising one or more N-acetyl-glucosaminyl, N-acetyl-lactosaminyl and/or lacto-N-biosyl groups; any of the N-acetyl-lactosaminyl and lacto-N-biosyl groups can be substituted with one or more fucosyl residues, $R_4$ is selected from H, N-acetyl-glucosaminyl and N-acetyl-lactosaminyl groups, wherein the N-acetyl-lactosaminyl group can be optionally substituted with a glycosyl residue comprising one or more N-acetyl-glucosaminyl, N-acetyl-lactosaminyl and/or one or more lacto-N-biosyl groups; any of the N-acetyl-lactosaminyl and lacto-N-biosyl groups can be substituted with one or more fucosyl residues;

even more preferably, formula 1 can be characterized by formula 1a, 1b or 1c

1a

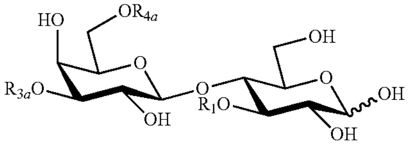

-continued

1b

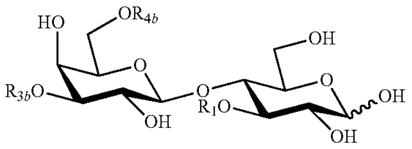

1c

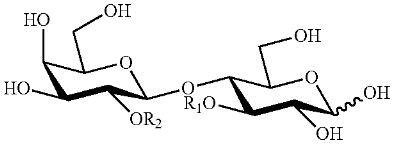

wherein $R_1$ and $R_2$ are as defined above, $R_{3a}$ is an N-acetyl-glucosaminyl group, or an N-acetyl-lactosaminyl group optionally substituted with a glycosyl residue comprising an N-acetyl-glucosaminyl, an N-acetyl-lactosaminyl and/or a lacto-N-biosyl group; any of the N-acetyl-lactosaminyl and lacto-N-biosyl groups can be substituted with one or more fucosyl residues, $R_{4a}$ is H, or an N-acetyl-glucosaminyl group, or an N-acetyl-lactosaminyl group optionally substituted with an N-acetyl-glucosaminyl or a lacto-N-biosyl group; any of the N-acetyl-lactosaminyl and lacto-N-biosyl groups can be substituted with one or more fucosyl residues, $R_{3b}$ is an N-acetyl-glucosaminyl group, or a lacto-N-biosyl group optionally substituted with a glycosyl residue comprising an N-acetyl-glucosaminyl, an N-acetyl-lactosaminyl and/or a lacto-N-biosyl group; any of the N-acetyl-lactosaminyl and lacto-N-biosyl groups can be substituted with one or more fucosyl residues, $R_{4b}$ is H, or an N-acetyl-glucosaminyl group, or an N-acetyl-lactosaminyl group optionally substituted with one or two N-acetyl-glucosaminyl, N-acetyl-lactosaminyl and/or one lacto-N-biosyl groups; any of the N-acetyl-lactosaminyl and lacto-N-biosyl groups can be substituted with one or more fucosyl residues;

still more preferably, the formulae 1a and 1b are characterized in that:

the N-acetyl-lactosaminyl group in the glycosyl residue of $R_{3a}$ is attached to another N-acetyl-lactosaminyl group with a 1-3 interglycosidic linkage, the lacto-N-biosyl group in the glycosyl residue of $R_{3a}$ is attached to the N-acetyl-lactosaminyl group with a 1-3 interglycosidic linkage, the lacto-N-biosyl group in the glycosyl residue of $R_{4a}$ is attached to the N-acetyl-lactosaminyl group with a 1-3 interglycosidic linkage, the N-acetyl-lactosaminyl group in the glycosyl residue of $R_{4b}$ is attached to another N-acetyl-lactosaminyl group with a 1-3 or a 1-6 interglycosidic linkage, the lacto-N-biosyl group in the glycosyl residue of $R_{4b}$ is attached to the N-acetyl-lactosaminyl group with a 1-3 interglycosidic linkage.

Yet more preferably, the compounds according to formulae 1a, 1b and 1c are human milk oligosaccharides, notably the preferred compounds of formula 1a are lacto-N-neotetraose, para-lacto-N-hexaose, para-lacto-N-neohexaose, lacto-N-neohexaose, para-lacto-N-octaose or lacto-N-neooctaose, all of which can optionally be substituted with one or more fucosyl residues; and the preferred compounds of formula 1b are lacto-N-tetraose, lacto-N-hexaose, lacto- N-octaose, iso-lacto-N-octaose, lacto-N-decaose or lacto-N-neodecaose, all of which can optionally be substituted with one or more fucosyl residues. Particularly, compounds of formula 1a or 1b are characterized in that the fucosyl residue attached to the N-acetyl-lactosaminyl and/or the lacto-N-biosyl group is linked to the galactose of the lacto-N-biosyl group with 1-2 interglycosidic linkage and/or the N-acetyl-glucosamine of the lacto-N-biosyl group with 1-4 interglycosidic linkage and/or the N-acetyl-glucosamine of the N-acetyl-lactosaminyl group with 1-3 interglycosidic linkage.

According to the most preferred aspect, the compounds of subformulae 1a, 1b and 1c are selected from the group of: lactose, 2'-fucosyllactose, 3-fucosyllactose, 2',3-difucosyllactose, lacto-N-tetraose, lacto-N-neotetraose, LNFP I, LNFP II, LNFP III, LNFP V, LNFP VI, LNDFH I, LNDFH II, LNDFH III, pLNnH, monofucosylated pLNnH, pLNH II, monofucosylated pLNH II and lacto-N-triose II.

In one embodiment, one of the first and the second hydrophilic neutral oligosaccharides does not comprise a GlcNAc or GalNAc unit in its structure, whereas the other does.

In one embodiment, both the first and the second hydrophilic neutral oligosaccharide comprise GlcNAc or GalNAc unit in their structure, preferably a GlcNAc unit.

In one embodiment, one of the first and the second hydrophilic neutral oligosaccharides comprises more GlcNAc or GalNAc units in its structure, preferably GlcNAc unit, than the other. According to a preferred embodiment, the first and the second oligosaccharides are characterized by formula 1a, more preferably $R_1$ is H, $R_{3a}$ is an N-acetyl-lactosaminyl group optionally substituted with an N-acetyl-lactosaminyl and/or a lacto-N-biosyl group; any of the N-acetyl-lactosaminyl and lacto-N-biosyl groups can be substituted with one or more fucosyl residues, and $R_{4a}$ is H. Even more preferably, one of the oligosaccharides is a tetrasaccharide, e.g. LNnT, and the other is a penta- or hexasaccharide, e.g. pLNnH. According to another preferred embodiment, the first and the second oligosaccharides are characterized by formula 1b, more preferably $R_1$ is H, $R_{3b}$ is a lacto-N-biosyl group optionally substituted with a glycosyl residue comprising an N-acetyl-glucosaminyl, an N-acetyl-lactosaminyl and/or a lacto-N-biosyl group; any of the N-acetyl-lactosaminyl and lacto-N-biosyl groups can be substituted with one or more fucosyl residues, and $R_{4b}$ is H. Even more preferably, one of the oligosaccharides is a tetrasaccharide, e.g. LNT, and the other is a penta- or hexasaccharide, e.g. pLNH II.

EXAMPLES

General: Before use, PS-DVB or BPS-DVB resins were mixed in 30% acetic acid solution for 2 hours and thereby degassed. Then they were filled in a glass column and washed with water until a conductivity of less than 500 μS/cm was reached.

Example 1

Two glass columns (l: 40 cm, d: 26 mm) were filled with Purosorb PAD428 BPS-DVB resin and Sepabeads SP825L PS-DVB (non-brominated) resin, respectively. A solution of a mixture of LNnT (500 mg) and pLNnH (115 mg, a ratio of 4.35:1) dissolved in 10 ml of water was chromatographed on each resin with a flow rate of ≈2.5 ml/min. Fractions (≈20 ml) were collected and analysed by HPLC.

Results:

For Purosorb PAD428 brominated PS-DVB resin, fractions 3-10 (96 ml, ≈0.5-1.67 bed volumes) were pooled that contained LNnT:pLNnH in a ratio of 8.7:1 (77% of LNnT was recovered).

For Sepabeads SP825L PS-DVB resin, fractions 2-8 (104 ml, ≈0.3-1.17 bed volumes) were pooled that contained LNnT:pLNnH in a ratio of 4.7:1 (98% of LNnT was recovered).

While the BPS-DVB resin enriched the LNnT by doubling its ratio, the non-brominated PS-DVB resin showed practically no separation.

Example 2

A glass column (1: 40 cm, d: 26 mm) was filled with Purosorb PAD428 BPS-DVB resin. A solution of a mixture of LNnT (1.2 g) and pLNnH (0.25 g, a ratio of 4.8:1) dissolved in 20 ml of water was chromatographed with a flow rate of ≈4 ml/min. Fractions (≈30 ml) were collected and analysed by HPLC.

Fractions 2-10 (240 ml, ≈0.5-2.6 bed volumes) were pooled that contained LNnT:pLNnH in a ratio of 7.65:1, whereas the LNnT was recovered in 90%.

Example 3

A glass column (1: 40 cm, d: 26 mm) was filled with Sepabeads SP207 BPS-DVB resin. A solution of a mixture of LNnT (1.5 g), pLNnH (100 mg) and F-pLNnH (Galβ1-4[Fucα1-3]GlcNAcβ1-3Galβ1-4GlcNAcβ1-3Galβ1-4Glc, see WO 2016/063261, 50 mg; a ratio of 30:2:1) dissolved in 30 ml of water was chromatographed with a flow rate of ≈6 ml/min. Fractions (≈30 ml) were collected and analysed by HPLC.

Fractions 3-14 (400 ml) were pooled that contained LNnT:pLNnH:Galβ1-4[Fucα1-3]GlcNAcβ1-3Galβ1-4GlcNAcβ1-3Galβ1-4Glc in a ratio of 129:2.6:1.

Example 4

LNnT was made by fermentation using a genetically modified *E. coli* cell of $LacZ^-$, $LacY^+$ phenotype, wherein said cell comprises a recombinant gene encoding a β-1,3-N-acetyl-glucosaminyl transferase which is able to transfer the GlcNAc of UDP-GlcNAc to the internalized lactose, a recombinant gene encoding a β-1,4-galactosyl transferase which is able to transfer the galactosyl residue of UDP-Gal to the N-acetyl-glucosaminylated lactose, and genes encoding a biosynthetic pathway to UDP-GlcNAc and UDP-Gal. The fermentation was performed by culturing said cell in the presence of exogenously added lactose and a suitable carbon source, thereby producing LNnT which was accompanied by lacto-N-triose II, pLNnH and lactose in the fermentation broth. The broth was subjected to a standard cell removal operation by UF, NF with diafiltration, decolourization with activated charcoal and ion exchange treatment (both cationic and anionic). The obtained solution contained LNnT (30 g/1), lactose, lacto-N-triose II and pLNnH (10.6% vs. LNnT). The solution was loaded on a column filled with Sepabeads SP207 BPS-DVB resin (approx. 1.6 g LNnT per 100 ml bed volume) and eluted with water containing 0.02% of isopropanol. Fractions of ≈1.1-2.1 bed volumes were collected. HPLC analysis showed that 82% of LNnT were recovered and the amount of pLNnH was reduced to 0.3% vs. LNnT.

Example 5

LNT was made by fermentation using a genetically modified *E. coli* cell of $LacZ^-$, $LacY^+$ phenotype, wherein said cell comprises a recombinant gene encoding a β-1,3-N-acetyl-glucosaminyl transferase which is able to transfer the GlcNAc of UDP-GlcNAc to the internalized lactose, a recombinant gene encoding a β-1,3-galactosyl transferase which is able to transfer the galactosyl residue of UDP-Gal to the N-acetyl-glucosaminylated lactose, and genes encoding a biosynthetic pathway to UDP-GlcNAc and UDP-Gal. The fermentation was performed by culturing said cell in the presence of exogenously added lactose and a suitable carbon source, thereby producing LNT which was accompanied by lacto-N-triose II, pLNH II and lactose in the fermentation broth. The broth was subjected to a standard cell removal operation by UF, NF with diafiltration, decolourization with activated charcoal and ion exchange treatment (both cationic and anionic). The obtained solution contained LNT (20.7 g/kg, purity by HPLC: 76.1%), lactose, lacto-N-triose II and pLNH II (3.23% vs. LNT). The solution was freeze-dried. A sample of the freeze-dried powder (3.40 g) was dissolved in 45 ml of water and the solution was loaded on a column filled with Sepabeads SP207 BPS-DVB resin (column diameter: 1.6 cm, bed volume: 170 ml) and eluted with water (1.5 bed volumes) then 20% methanol. Fraction volume was 170 ml. Fractions 11-26 were pooled and freeze-dried yielding 2.85 g of a solid. HPLC analysis showed that purity of LNT was increased to 81.3% whereas the amount of pLNH II was reduced to 0.25% vs. LNT.

The invention claimed is:

1. A method for separating a first human milk oligosaccharide (HMO) from a second HMO comprising subjecting an aqueous solution comprising the first and the second HMO to reverse phase chromatography on a bromine functionalized polystyrene cross-linked with divinylbenzene (BPS-DVB) stationary medium, wherein the second HMO is a tetrasaccharide and the first HMO is a hexa- or heptasaccharide, and wherein the first HMO and the second HMO comprise a GlcNAc-moiety.

2. The method according to claim 1, wherein level of bromination of the BPS-DVB medium is about 25-61 w/w % per dry weight.

3. The method according to claim 1, wherein the first HMO and the second HMO are produced intracellularly by fermentation in an aqueous culture medium.

4. The method according to claim 3, wherein the chromatography on the BPS-DVB medium is preceded by at least one of the following steps:

a) clarifying the aqueous culture medium to remove therefrom particulates and contaminants from a fermentation process, to provide a clarified aqueous medium, b) removing substantially all proteins from the aqueous medium to provide a protein-free aqueous medium, or c) removing salts and charged components from the aqueous culture medium, from the clarified aqueous medium of step a), or from the protein-free aqueous medium of step b).

5. The method according to claim 4, wherein steps a), b) and/or c) comprise at least one of ultrafiltration, nanofiltration, or ion exchange treatment.

6. The method according to claim 1, wherein one of the HMOs comprises more GlcNAc-moieties than the other HMO.

7. The method according to claim 6, wherein the first HMO comprises more GlcNAc-moieties than the second HMO.

8. The method according to claim 1, wherein the tetrasaccharide is LNnT and the hexasaccharide is pLNnH.

9. The method according to claim 1, wherein the tetrasaccharide is LNT and the hexasaccharide is pLNH II.

10. The method according to claim 2, wherein level of bromination of the BPS-DVB medium is about 25-35 w/w % per dry weight.

11. The method according to claim 5, further comprising an activated charcoal treatment.

* * * * *